United States Patent
Drzewiecki et al.

(10) Patent No.: US 8,314,286 B2
(45) Date of Patent: Nov. 20, 2012

(54) FLEXIBLE LIQUID ABSORBING STRUCTURE

(75) Inventors: Brian Michael Drzewiecki, Princeton, NJ (US); Joseph M. Luizzi, Newtown, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 1079 days.

(21) Appl. No.: 10/444,605

(22) Filed: May 23, 2003

(65) Prior Publication Data

US 2004/0236294 A1  Nov. 25, 2004

(51) Int. Cl.
*A61F 13/15* (2006.01)
*A61F 13/20* (2006.01)

(52) U.S. Cl. ......................................... 604/368

(58) Field of Classification Search ............... 524/916; 604/366, 368, 367; 442/394
See application file for complete search history.

(56) References Cited

U.S. PATENT DOCUMENTS

| | | | |
|---|---|---|---|
| 3,339,546 A * | 9/1967 | Chen | 602/56 |
| 4,963,861 A | 10/1990 | Thioulouse et al. | |
| 5,609,588 A | 3/1997 | DiPalma et al. | |
| 5,807,367 A | 9/1998 | Dilnik et al. | |
| 5,853,867 A * | 12/1998 | Harada et al. | 428/317.9 |
| 2005/0130542 A1 | 6/2005 | Klein | |

FOREIGN PATENT DOCUMENTS

| | | |
|---|---|---|
| AU | 04249116 | 12/2004 |
| CA | 2469626 | 6/2003 |
| CN | 1261090 | 7/2000 |
| EP | 1013291 A1 * | 6/2000 |
| JP | 00201975 | 7/2000 |
| JP | 2000204333 | 7/2000 |
| JP | 2002526560 | 8/2002 |
| WO | WO 99/57201 A | 11/1999 |
| WO | WO 02/07791 A | 1/2002 |
| WO | WO 03/049777 | 6/2003 |
| WO | WO 03/052188 | 6/2003 |
| WO | WO 2004/112849 | 12/2004 |

OTHER PUBLICATIONS

International Search Report for Appln. No. PCT/US2004/015750 dated Dec. 27, 2005.

* cited by examiner

*Primary Examiner* — Melanie Hand (57) ABSTRACT

A thin, flexible absorbent structure comprising a flexible substrate and an aqueous liquid absorbing material disposed on said substrate, wherein said aqueous liquid absorbing material comprises a homogeneous mixture of a hot melt adhesive and an aqueous liquid absorbing polymer, wherein the aqueous liquid absorbing polymer is present in the mixture in an amount greater than 1% by weight of the mixture and the aqueous liquid absorbing structure has an absorbency greater than about 5 g/g, and a Gurley Stiffness less than about 400 mg and a caliper less than about 4 mm.

1 Claim, 6 Drawing Sheets

FLEXIBLE LIQUID ABSORBING STRUCTURE

FIELD OF THE INVENTION

The present invention relates generally to a thin, flexible aqueous liquid absorbing structure having improved absorbency characteristics and, in particular, to absorbent articles such as sanitary napkins, pantiliners and wound dressings containing the structure.

BACKGROUND OF THE INVENTION

Sanitary absorbent articles find wide and varied use in absorbing and trapping body fluids and maintaining body surfaces in a state of dryness and comfort. Such articles find use, for example in wound coverings and in sanitary protection devices. These articles generally include a liquid permeable layer which is placed nearest the body surface of the wearer and which may be an absorbent material serving as the main repository for liquid absorbed by the article. The article may be a multi-layer article having a liquid permeable layer, a separate aqueous liquid absorbing material underlying the liquid permeable layer and a liquid impermeable layer impervious to liquid absorbed into the absorbent material and serving as a protective barrier between the absorbent material and the wearer's clothing. The articles may also include an acquisition or transfer layer with a relatively open structure having a relatively high void volume for accepting and transporting the liquid to the absorbent core. The aqueous liquid absorbing material typically has a high liquid absorption capacity relative to the liquid permeable layer and transfer layer and can be made from materials such as wood pulp, creped cellulose wadding, absorbent foams and sponges, polymeric fibers, aqueous liquid absorbing polymers and combinations of these materials.

Conventional sanitary absorbent articles have an absorbent structure formed of cellulosic fibers such as cotton, wood pulp or rayon, mixtures of cellulosic and synthetic fibers such as polyethylene/polyester bicomponent fibers. These absorbent structures, in order to provide the requisite absorbency, are generally fairly thick (greater than 5 mm). The thickness of such an article can cause a high degree of wearing awareness, frequently resulting in user discomfort and/or poor fit between wearer's body surface and clothing. Although somewhat flexible and conforming to the body, thick sanitary absorbent articles frequently tend to deform or bunch in use, with further discomfort to the wearer and the possibility of loss of absorbency where it is most needed. When an article with this absorbent structure is subjected to a compressive load typically experienced in use, the structure can collapse resulting in liquid being expressed from the absorbent material and rewetting the layers through which liquid was originally routed to the absorbent structure. Since typical transfer layers and liquid permeable body surface facing layers are generally made from materials with little absorption capacity, the liquid expelled from the absorbent structure will tend to reside next to the body surface of the wearer resulting in discomfort and possible staining of the wearer's garments.

One solution to this problem utilizes aqueous liquid absorbing polymers, also known as superabsorbents, in the absorbent structure. The development of materials having a high aqueous liquid absorption capacity per unit volume has allowed the required overall thickness of absorbent articles to be reduced providing products which are less obtrusive to wear. Combination of aqueous liquid absorbing polymers with fibrous absorbents has resulted in development of absorbent articles which are relatively thin, i.e. less than 3 mm, and which generally retain absorbed fluid when subjected to compressive loads encountered in wearing the article. For example, U.S. Pat. No. 4,217,901 to Bradstreet and Roller discloses a thin sanitary napkin having a thickness from about 3.0 to about 7.0 mm and comprising a densified absorbent layer containing particulate superabsorbent.

However, when the aqueous liquid absorbing polymer is a particulate superabsorbent that is not well anchored in the absorbent structure, the particles can migrate within the structure or fall out of the article resulting in loss of absorbent capacity or variation in absorbency throughout the absorbent article. This can result in liquid and/or superabsorbent particles residing next to the body surface of the wearer; again, resulting in discomfort and possible staining of the wearers' garments.

To be most effective, an absorbent article needs to have the absorbent structure located in the region of the absorbent article where it will be most effective in absorbing and retaining liquids and the absorbent components need to be anchored within the structure.

Typically hot melt adhesives are used in the construction of an absorbent article to attach layers to one another and to adhesively fix the liquid impermeable backsheet to the liquid permeable topsheet around a peripheral edge margin to form a flange seal and thereby fully enclose the absorbent structure. Hot melt adhesives are also used in the construction of absorbent structures to laminate multiple plies together or to adhesively fix superabsorbent particles to fibrous components of the structure. Some problems encountered with absorbent-articles constructed in this way include stiffness or inflexibility of the article, hot melt adhesive blocking passage of liquid through the article to the absorbent structure and superabsorbent particles coated with the non-absorbent hot melt adhesive. U.S. Pat. No. 6,458,877 to Ahmed discloses compositions comprising at least one thermoplastic component, at least one diluent having polar functionality and at least one superabsorbent polymer. Also, European Patent Application EP-1013291 to Luizzi describes hot melt adhesives capable of absorbing liquid that are useful in construction of absorbent products and also describes an absorbent element containing hot melt adhesive comprising an aqueous liquid absorbing polymer.

There exists a need for an aqueous liquid absorbing structure, that is very thin, i.e. having a caliper less than 4 mm, very absorbent, i.e. having an absorbency greater than 5 g/g, and very flexible, i.e. having a Gurley stiffness less than 400 mg.

When the resulting absorbent article is a sanitary napkin or a pantiliner, it is freely adaptable both to the undergarment and to the body of the user. When the absorbent article is a wound covering, it is adaptable to the skin of the user and does not limit movement of the body part covered. Applicants have surprisingly discovered such a structure, which is described herein

SUMMARY OF THE INVENTION

In accordance with the present invention there has been provided a thin flexible aqueous liquid absorbing structure comprising a flexible substrate having a first surface and a second surface and an aqueous liquid absorbing material disposed on at least a portion of said first surface of the flexible substrate. The aqueous liquid absorbing material comprises a homogeneous mixture of a hot melt adhesive and an aqueous liquid absorbing polymer. The aqueous liquid absorbing polymer is present in the mixture in an amount greater than 1% by weight of the mixture to provide an absorbency greater than about 5 grams per gram (g/g) and the aqueous liquid absorbing structure has a Gurley stiffness less than about 400 mg and a caliper less than about 4 mm.

Also provided in accordance with the invention is an absorbent article for feminine hygiene adapted for placement in a crotch portion of an undergarment, and comprising: a liquid permeable body faceable layer; a liquid impermeable garment faceable layer and an aqueous liquid absorbing material between said body faceable layer and said garment faceable layer wherein the aqueous liquid absorbing material comprises a homogenous mixture of a hot melt adhesive and an aqueous liquid absorbing polymer. The aqueous liquid absorbing polymer is present in the mixture in an amount greater than 5% by weight of the mixture and the absorbent article is characterized by an absorbency greater than about 5 g/g, a Gurley stiffness less than about 400 mg and a caliper less than about 4 mm.

In another embodiment provided in accordance with the invention is an absorbent article for feminine hygiene adapted for placement in a crotch portion of an undergarment and having a longitudinal axis. The absorbent article comprises a liquid permeable body faceable layer, a liquid impermeable garment faceable layer, an absorbent element positioned between said body faceable layer and said garment faceable layer and a peripheral zone aligned adjacent to one of said longitudinal edges of said absorbent zone. The absorbent element has a longitudinally extending central absorbent zone aligned along the longitudinal axis of said absorbent article and has two opposing longitudinal edges and two opposing transverse edges. The peripheral zone comprises the body faceable layer, the garment faceable layer and an aqueous liquid absorbing material therebetween. The aqueous liquid absorbing material comprises a homogeneous mixture of a hot melt adhesive and an aqueous liquid absorbing polymer, wherein said aqueous liquid absorbing polymer is present in the mixture in an amount greater than 5% by weight of the mixture, said peripheral zone being characterized by an absorbency greater than about 5 g/g and a thickness less than about 4 mm. The central absorbent zone and the peripheral zone have a respective Gurley stiffness wherein the Gurley stiffness of the peripheral zone is less than the Gurley stiffness of the central absorbent zone.

Yet another embodiment provided in accordance with the invention is an absorbent article adapted for use as a wound covering and comprising a flexible backing layer having a first surface and a second surface, and a wound faceable aqueous liquid absorbing material disposed on at least a portion of the first surface of the backing layer. The aqueous liquid absorbing material comprises a homogeneous mixture of a hot melt adhesive and an aqueous liquid absorbing polymer, wherein the aqueous liquid absorbing polymer is present in the mixture in an amount greater than 1% by weight of the mixture; and the absorbent zone is characterized by an absorbency greater than about 5 g/g, a Gurley stiffness less than about 250 mg and a caliper less than about 2 mm.

Other aspects and features of the present invention will become apparent to those ordinarily skilled in the art upon review of the following description of specific embodiments of the invention in conjunction with the accompanying drawings.

BRIEF DESCRIPTION OF THE DRAWINGS

While the specification concludes with claims particularly pointing out and distinctly claiming the present invention, it is believed that the present invention will be better understood from the following description in conjunction with the following drawings, in which like reference numbers identify identical elements and component thicknesses have been exaggerated for ease of illustration wherein:

DETAILED DESCRIPTION OF THE INVENTION

The present invention is directed to a thin, flexible aqueous liquid absorbing structure designed to conform to the surface to which it is applied, remain flexible in use and that is useful for absorbing and trapping bodily fluids. More particularly, the present invention provides absorbent articles for feminine hygiene or wound covering which comprise said structure and which are thin and flexible and offer enhanced fit, comfort, and containment As used herein, the term "sanitary napkin" refers to an article which is worn by females adjacent to the pudendal region and which is intended to absorb and contain the various exudates which are discharged from the body (e.g., blood, menses and urine) and which is intended to be discarded after a single use (i.e., it is not intended to be laundered or otherwise restored or reused). As used herein, the term "pudendal" refers to the externally visible female genitalia and is limited to the labia majora, the labia minora, the clitoris, and the vestibule. Interlabial devices which reside within or partially within and partially external of the wearers vestibule are also within the scope of this invention. Sanitary napkins designed to fit specialty undergarments such as thong underwear are also included.

Figure 1:
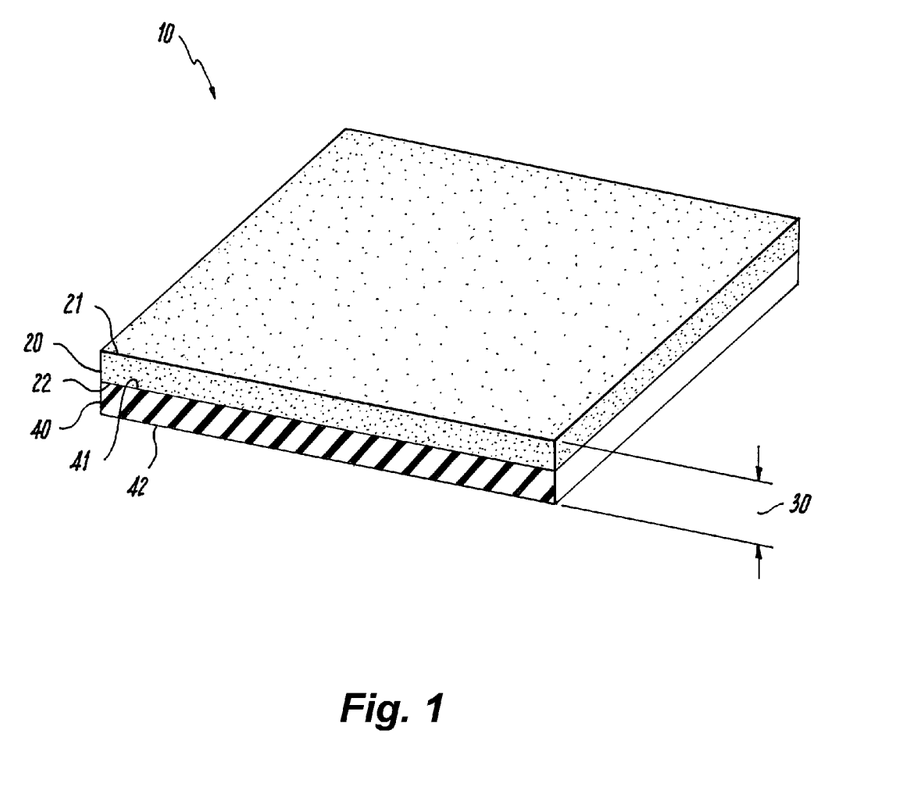
FIG. 1 is a perspective view of a flexible aqueous liquid absorbing structure of the present invention.

Referring to FIG. 1, there is shown an embodiment of the present invention, a flexible aqueous liquid absorbing structure 10 comprising a flexible substrate 40 having a first surface 41 and a second opposing surface 42, and aqueous liquid absorbing material 20 having opposing surfaces 21, 22 wherein surface 22 is disposed on surface 41 of flexible substrate 40. In the embodiment of the invention shown in FIG. 1, the aqueous liquid absorbing material 20 comprises a homogeneous mixture of an absorbent hot melt adhesive and an aqueous liquid absorbing polymer wherein the aqueous liquid absorbing polymer is present in the mixture in an amount greater than 1% by weight of the mixture and is disposed as a continuous layer on substrate 40 in the structure 10. The aqueous liquid absorbing structure 10 has absorbency greater than about 5 grams per gram (g/g) and Gurley stiffness less than about 400 mg.

As used herein, the terminology "thin" refers to the caliper of the absorbent structure 10 or of the area comprising the absorbent structure in an absorbent article. Caliper is defined as the distance 30 between the two opposing outermost surfaces 21, 42 of the structure; or, in an article comprising the structure, caliper is measured in an area of the article which contains the absorbent structure. For example, in an embodiment in which an area of the article consists of cover, transfer layer, aqueous liquid absorbing material and barrier layer; while other areas of the article may consist solely of cover, transfer layer, absorbent element and barrier layer; the caliper would be measured in the area containing the aqueous liquid absorbing material. The procedure for measuring caliper is given in the Test Methods section. Preferably the caliper of structures of the present invention is less than about 4 mm. More preferably the caliper is less than about 3 mm and even more preferably the caliper is less than about 2 mm.

As used herein, the term "flexible" refers to the ability of the absorbent structure to conform to the contours of the human body and is defined as the Gurley stiffness of a structure. Gurley stiffness measures the bendability or flexibility of absorbent materials. In general, the lower the Gurley stiffness value, the more flexible the material. The procedure for measuring Gurley stiffness is given in the Test Methods section. The structures of the present invention have a Gurley Stiffness less than about 400 mg, preferably less than about 250 mg and even more preferably less than about 100 mg.

Extremely flexible structures can be referred to as drapeable. The terms "drapeable" and "drapability" are used interchangeably and mean having a flexural resistance of about 35 grams (g) or less as tested by the Modified Circular Bend Test, ASTM 4032-82 as set forth in the Example section of U.S. patent application Ser. No. 09/477,244 to Brisebois, et al, filed Jan. 4, 2000 and incorporated herein by reference. Drapeable articles comprising the aqueous liquid absorbing material of the present invention have also been found to have a flexural resistance of about 35 g or less.

All ranges used herein expressly include at least all numbers that fall between the endpoints of ranges.

As used herein, the terminology "absorbency" of a structure of the present invention refers to the free swell absorbency, in grams per gram (g/g), as measured by the Tea Bag Test detailed in the Test Method section. The absorbency of structures of the present invention is greater than about 5 g/g, preferably greater than about 15 g/g, more preferably is greater than about 35 g/g.

Figure 2:
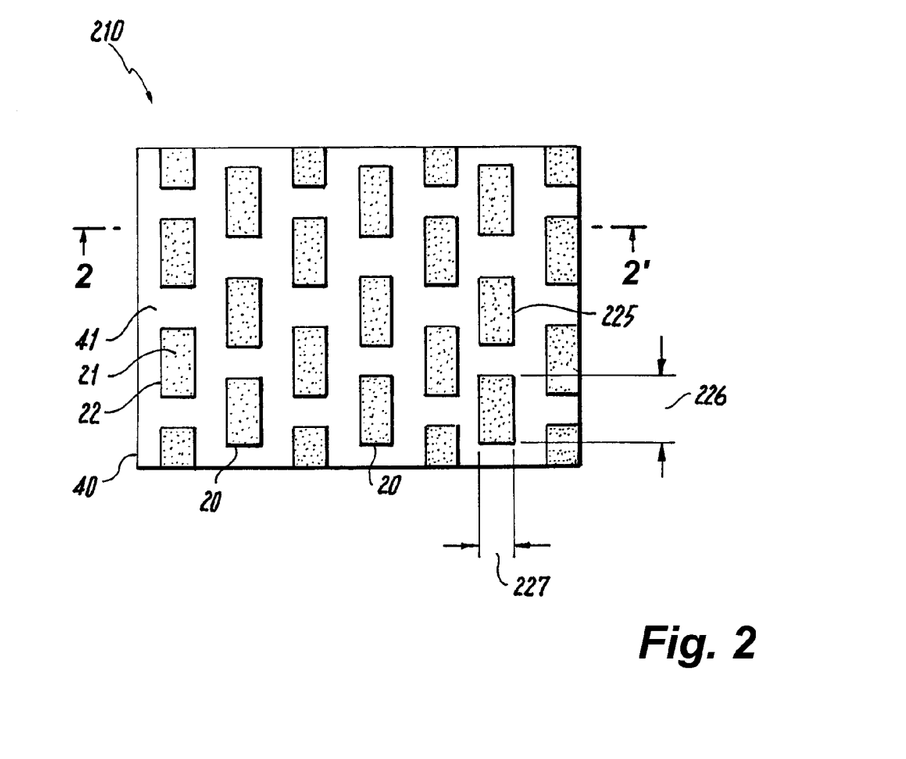
FIG. 2 is a top plan view of another embodiment of the flexible aqueous liquid absorbing structure of the present invention.

Referring now to FIG. 2, there is shown yet another embodiment of the present invention in a top plan view in which the flexible aqueous liquid absorbing structure 210 comprises aqueous liquid absorbing material 20 disposed on surface 41 of flexible substrate 40 in an arrangement of discrete elements 225. By discrete is meant that each individual element 225 of the aqueous liquid absorbing material 20 is separated from all other elements 225 on the surface of the flexible substrate.

Figure 3:
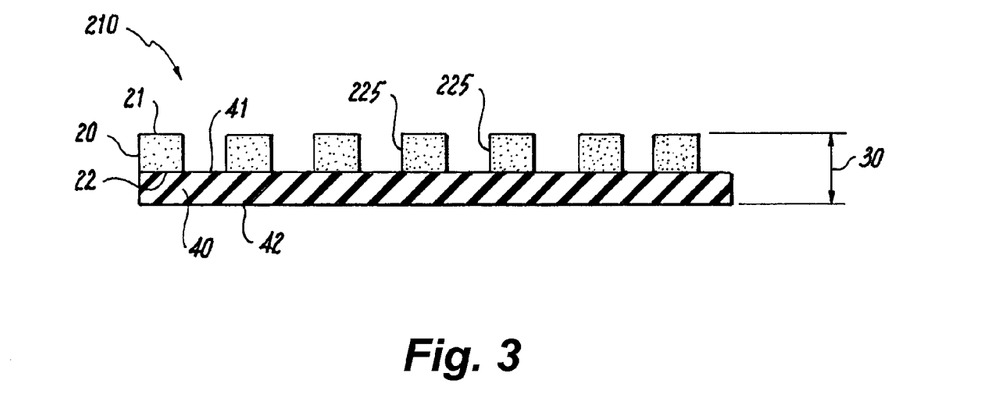
FIG. 3 is an end view of the embodiment shown in FIG. 2 as taken along section line 2-2' of FIG. 2.

FIG. 3 shows the embodiment of FIG. 2 in a side elevation view along the section line 2-2'. Although the discrete elements are shown in FIGS. 2 and 3 as a staggered array of rectangular elements 225, it will be readily apparent to one skilled in the art that any of a wide variety of shapes and pattern arrangements is possible.

Referring now to FIGS. 1-3, the aqueous liquid absorbing material 20 comprises an absorbent hot melt adhesive containing greater than about 1% by weight of an aqueous liquid absorbing polymer. Additionally, each of the aqueous liquid absorbing structures 10 and 210 has an absorbency greater than about 5 grams per gram as measured by the Tea Bag Method and a Gurley stiffness less than about 400 mg. The structures 10 and 210 also have a thickness or caliper 30 less than about 4 mm.

The inventors have found that aqueous liquid absorbing structures capable of successfully absorbing body fluids while remaining completely conformable and unobtrusive in use should have an absorbency greater than about 5 g/g, a Gurley stiffness less than about 400 mg and a caliper less than about 4 mm. Preferably, the structures 10 and 210 have a caliper less than about 3 mm and more preferably less than about 2 mm. A caliper less than about 1 mm. has been found to be particularly useful for embodiments of the present invention adapted for use as a wound covering.

The flexible substrate 40 in embodiments of the present invention can be either aqueous liquid impermeable or permeable, depending on the desired end use for the structures 10, 210. Where the flexible aqueous liquid absorbing structure is designed to absorb liquid and prevent transfer of the liquid beyond the structure, as, for example in a sanitary napkin, an aqueous liquid impermeable material that prevents and/or retards the through transfer of liquid but does not necessarily prevent the passage of gases may be used for the flexible substrate 40. Suitable preferred materials include polyethylene or polypropylene films. Other materials that may be used as the liquid impermeable layer include films of polyesters, polyamides, ethylene vinyl acetate, polyvinyl chloride, polyvinylidene chloride, cellophane, nitrocellulose and cellulose acetate. Co-extruded and laminated combinations of the foregoing, wherein such combinations are permitted by the chemical and physical properties of the film, may be used. Liquid impermeable reticulated foams may also be used. Adhesive coatings, for positioning structures 10, 210 in a user's undergarments, may also serve as the liquid impermeable layer.

Liquid impermeable layers that block or retard liquid permeation, but permit gases to transpire, i.e., "breathable barriers", may also be used as the flexible substrate 40. Single or multiple layers of microporous films, fabrics and combinations thereof, that provide a tortuous path, and/or whose surface characteristics provide a liquid repellent surface to the penetration of liquids may be used to provide such breathable barriers. A nonwoven web particularly useful as a breathable, liquid impermeable layer is a spunbond polypropylene web, providing a retarding effect, but not necessarily an absolute barrier, to liquid strikethrough.

Where it is desirable for the flexible substrate 40 to be a body faceable layer, in use, which can pass liquid to the aqueous liquid absorbing material 20, an aqueous liquid permeable material is used as the substrate 40. In this case, the substrate 40 is preferably compliant, soft feeling, and non-irritating to a users skin. The substrate 40 should further exhibit good fluid strikethrough and a reduced tendency to rewet, permitting bodily discharges to rapidly penetrate it and flow toward subsequent underlying aqueous liquid absorbing material 20, while not allowing such discharges to flow back through the liquid permeable layer to the skin of the user. A suitable aqueous liquid permeable material may be manufactured from a wide range of materials including, but not limited to, woven and nonwoven fabrics, apertured formed polymeric films, porous foams, reticulated foams, reticulated thermoplastic films, and thermoplastic scrims. In addition, the liquid permeable substrate may be constructed from a combination of one or more of the above materials, such as a composite layer of nonwoven and apertured, formed polymeric film.

Particularly suitable liquid permeable materials include a thermobonded multidenier (3 and 5 denier) polypropylene nonwoven web, and a through-air bonded nonwoven comprising polyethylene sheath and polypropylene core bi-component fibers. The liquid permeable material may employ adhesives on its body faceable surface for attaching the structures 10, 210 directly to a users skin. Examples of adhesives suitable for body attachment include, but are not limited to styrene-ethylene-butadiene-styrene oil gels, polyethylene glycol-poly-HEMA, and silicones such as Dow Corning #9600.

The aqueous liquid absorbing material 20 comprises a homogeneous mixture of a hot melt adhesive containing greater than about 1% by weight of an aqueous liquid absorbing polymer. The liquid absorbing material is capable of absorbing and trapping liquid within the aqueous liquid absorbing polymer but is not soluble in the liquids absorbed. The material 20 may be formed by blending about 10% to 50% of a block copolymer; about 20% to 80% of a tackifying resin and greater than about 1% of an aqueous liquid absorbing polymer in suitable adhesive processing equipment such as a melt mixer or extruder at a temperature above their respective melting points until uniformly mixed. The amount of aqueous liquid absorbing polymer will define the absorbency of the material; the more aqueous liquid absorbing polymer added, the greater the absorbency.

Suitable block copolymers for use in the invention include linear or radial co-polymer structures having the formula $(A-B)_x$, wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalphamethylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.

Suitable tackifying resins include natural and modified resins; glycerol and pentaerythritol esters of natural and modified resins; polyterpene resins; copolymers and terpolymers of natural terpenes; phenolic modified terpene resins and the hydrogenated derivatives thereof; aliphatic petroleum resins and the hydrogenated derivatives thereof; aromatic petroleum resin and the hydrogenated derivatives thereof; and aliphatic or aromatic petroleum resins and the hydrogenated derivatives thereof, and combinations thereof. Commercial examples of these types of resins include Foral® hydrogenated rosin ester, Staybelite® hydrogenated modified rosin, Poly-pale® polymerized rosin, Permalyne rosin ester, Pentalyn® rosin ester, Adtac® oil extended hydrocarbon resin, Piccopale® aromatic hydrocarbon, Piccotac®, Hercotac® aromatic modified aliphatic hydrocarbon, Regalreze® cycloaliphatic resins, or Piccolyte® from Hercules, Eselementz® from Exxon Chemical aliphatic hydrocarbon and cycloaliphatic resins, Wingtack® from Goodyear Tire & Rubber Co. synthetic polyterpene resins including aromatic modified versions, Arkon® partially and fully hydrogenated aromatic resins from Arakawa Chemicals, Zonatac® styrenated terpene resin, Zonarez® rosin ester and Zonester® rosin ester from Arizona Chemical and Nevtac® aromatic modified aliphatic hydrocarbon from Neville Chemical Company.

Aqueous liquid absorbing polymers suitable for inclusion in the aqueous liquid absorbing material 20 include thermoplastic hydrogels such as superabsorbent materials or thermoplastic polymeric compositions, which are formed from a water-soluble soft segment and one or more hard segments. The hard segment must be melt processable, i.e. at use temperature the hard segments in the polymer are below their melt temperature, and at process temperature, the hard segments are above their melting point temperature and below the decomposition temperature of either the other components of the hot-melt adhesive composition. The hard segment is substantially insoluble in water, and phase separates from the soft segment. Examples of suitable hard segments include, but are not limited to polyurethane, polyamides, polyesters, polyureas, and combinations thereof. Examples of suitable soft segments include, but are not limited to polyethylene oxide, polyvinyl alcohol, polyvinyl pyrrolidone, polyacrylamide, polysaccharide, polymaleic anhydride, random copolymers of polyethylene oxide and polypropyleneoxide and combinations thereof. The soft and hard segments may be covalently bonded together by means of urethane, amide, ester, or secondary urea linkages or combinations thereof. Examples of aqueous liquid absorbing thermoplastic polymeric compositions which are commercially available include hydrophilic polyurethane from Tyndale Plains-Hunter Ltd. and Aquacaulk® thermoplastic polymers from Sumitomo Seika Chemicals Co., Ltd. Suitable superabsorbent materials include any of the conventional superabsorbent particles or superabsorbent fibers which are commercially available today Examples are Aquakeep SA-70 and J-550P from Sumitomo Seika Chemicals Co., Ltd. The superabsorbent material is preferably a superabsorbent particle having an average particle size less than about 150 microns. More preferably the superabsorbent particles have an average particle size less than about 125 microns. Most preferably, the superabsorbent particles have an average particle size less than about 75 microns. The small particle size of the aqueous liquid absorbing polymer results in increased absorbent polymer exposure at the surface of the aqueous liquid absorbing material and is essential for attaining a homogeneous mixture and for facilitating processing the material through conventional hot melt adhesive application equipment.

Suitable plasticizers for use in the present invention generally will include any conventional plasticizers which decrease hardness and modulus, enhance pressure sensitive tack and reduce melt and solution viscosity. It is preferred that the plasticizer be water soluble or water dispersible or alternatively be a wax-like substance such as polyethylene glycol, glycerin, glycerol, polypropylene glycol, butylene glycol or sorbitol. An example of a preferred plastizer is Carbowax® polyethylene glycol from Union Carbide.

Suitable anti-oxidants for use in the present invention include any conventional anti-oxidants, and are preferably hindered phenols such as for example Ethanox 330w 1,3,5-trimethyl-2,4,6-tris(3,5-di-tert-butyl4-hydroxybenzyl) benzene which is commercially available from the Ethyl Corporation.

In a preferred embodiment, the aqueous liquid absorbing material comprises (by weight): about 10-50% block copolymer, preferably with a melt index greater than about 10, about 20-80% tackifying resin, preferably with a softening point less than about 105° C., greater than about 1% aqueous liquid absorbing polymer, about 0-40% plasitcizer with viscosity from 1-500 centipoise at application temperature, and about 0-2.0% antioxidant.

The liquid absorbing material 20 may be applied to substrate 40 to form structures 10, 210 using suitable conventional adhesive processing equipment such as a hot melt adhesive slot coating head, a hot melt adhesive swirl spray applicator (a commercial example of which is a Nordson Control Fiberization®), using a hot melt adhesive micro fiber applicator (commercial examples of these applicators include Nordson Control Coat®, ITW Dynafiber®, J&M Meltblown, and May Coating's Accufiber®), using a hot melt adhesive rotary screen applicator to create a pattern coating (examples of this equipment include Nordson and Kraemer rotary screen technology).

Figure 4:
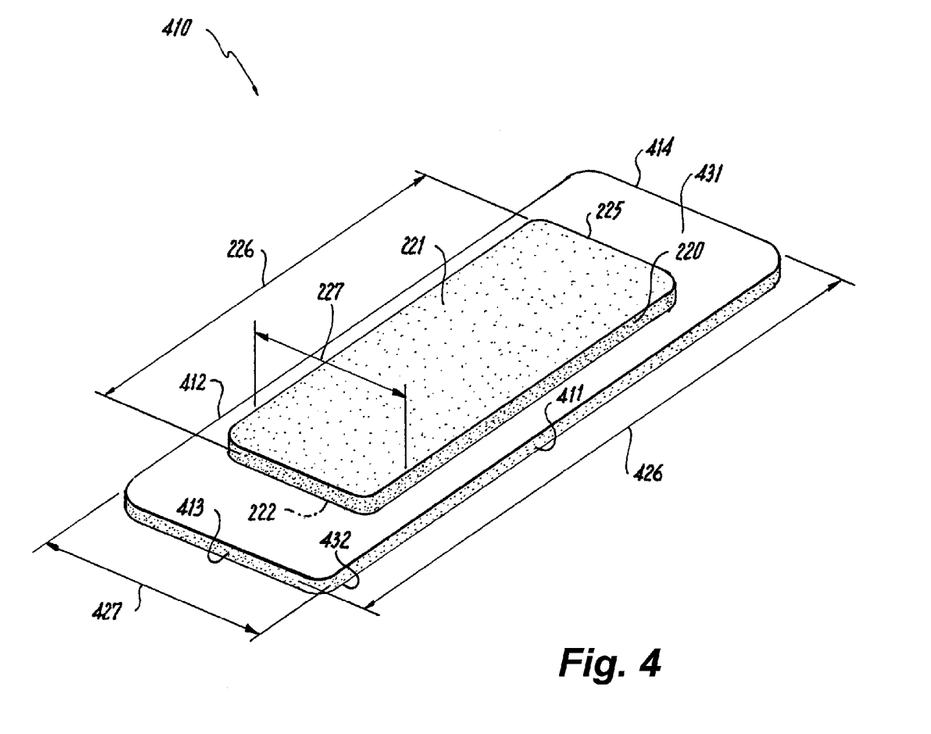
FIG. 4 is a perspective view of another embodiment of the flexible aqueous absorbing structure of the present invention.

Referring to FIG. 4, there is shown an embodiment of the present invention, a flexible aqueous liquid absorbing article 410 for absorbing body fluids, comprising a flexible substrate 430 having a first surface 431 and a second opposing surface 432, and aqueous liquid absorbing material 220 having opposing surfaces 221, 222 wherein surface 222 is disposed on surface 431 of flexible substrate 430. The article 410 has a length 426 and a width 427. In the embodiment of the invention shown in FIG. 4, the aqueous liquid absorbing material 220 comprises a homogeneous mixture of an absorbent hot melt adhesive and an aqueous liquid absorbing polymer wherein the aqueous liquid absorbing polymer is a particulate superabsorbent with average particle size less than about 150 microns. The aqueous liquid absorbing material 220 is disposed on flexible substrate 430 of article 410 as at least one discrete element 225, wherein said discrete element 225 is a rectangle having a length 226 and a width 227, wherein said length 226 is greater than said width 227 and wherein said length 226 of said discrete element 225 is disposed parallel to one of said longitudinal edges 411, 412 of said article 410. In another embodiment of the present invention the length 426 is greater than three times the width 427.

Figure 5:
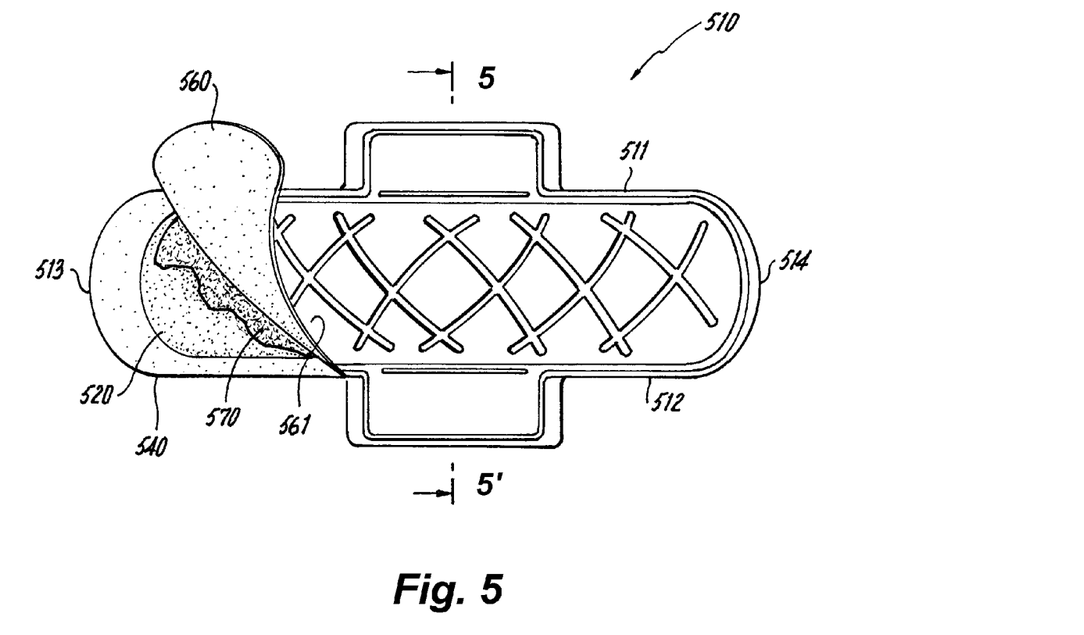
FIG. 5 is a top plan view of an absorbent article for feminine hygiene in accordance with the present invention, the body faceable layer of the article being partly removed to show the underlying structure.
Figure 6:
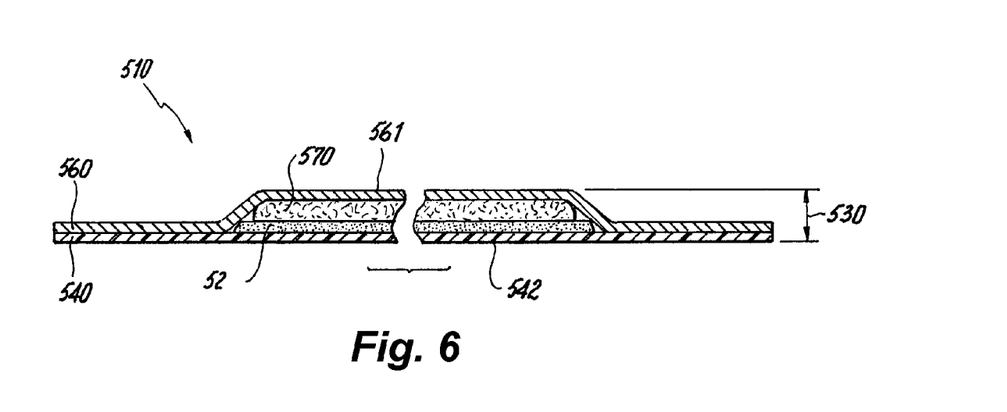
FIG. 6 is an end view of the embodiment shown in FIG. 5 as taken along section line 5-5' of FIG. 5.

Shown in FIGS. 5 and 6, is yet another embodiment of the invention, an absorbent article 510 for feminine hygiene adapted for placement in a crotch portion of an undergarment, said absorbent article 510 comprising: a liquid permeable body faceable layer 560 having a body faceable surface 561; a liquid impermeable garment faceable layer 540 having a garment faceable surface 542 and aqueous liquid absorbing material 520 between said body faceable layer 560 and said garment faceable layer 540. The aqueous liquid absorbing material 520 comprises a homogeneous mixture of a hot melt adhesive and an aqueous liquid absorbing polymer. The absorbent article has a Gurley stiffness less than 400 mg and a caliper 530 less than 4 mm. As shown in FIG. 6, the aqueous liquid absorbing material 520 is contiguous to and is partially covered by an optional transfer layer 570. The transfer layer 570 is preferably a fibrous nonwoven fabric capable of rapidly acquiring liquid from the liquid permeable body faceable layer 540 and retaining the liquid until the slower absorbing aqueous liquid absorbing material 520 absorbs the liquid. Examples of such absorbent articles are pantiliners or sanitary napkins including interlabial pads and sanitary napkins designed for a particular undergarment type, i.e. thong underwear. Pantiliners and sanitary napkins according to the present invention are unobtrusive and comfortable in use, conforming both to a user's undergarment and anatomy. In absorbent articles of the present invention the amount of aqueous liquid absorbing polymer in the aqueous liquid absorbing material 520 and the amount of the aqueous liquid absorbing material in the absorbent article can be varied to provide an absorbent article accommodating relatively small amounts of fluid, such as would be absorbed by a pantiliner, to an article with high absorbency needed for larger amounts of fluid, as in a sanitary napkin for overnight use.

For the sanitary napkin shown in FIGS. 5 and 6, attachment means (not shown) may occupy portions of the garment facing surface 542 of the liquid impermeable layer 540 and/or portions of the body facing surface 561 of liquid permeable layer 560. Adhesives (not shown) may be applied to surface 561 for attaching the liquid permeable layer directly to a user's body. Suitable body attaching adhesives have been detailed above.

Alternatively, positioning adhesives, mechanical fasteners, or high coefficient of friction materials may be applied to surface 542 for releaseably adhering the sanitary napkin of FIG. 5, 6 to a user's garment. Or, the barrier layer itself may be constructed from a high coefficient of friction material, such as natural or synthetic rubber, thereby eliminating the need for additional material to provide undergarment attachment. Preferably, positioning adhesives are used to adhere the sanitary napkin 510 to a crotch portion of a user's undergarments. Positioning adhesives suitable for sanitary napkins of the present invention are well known in the art, one known class being styrenic block copolymers. Techniques used for applying the adhesives to the sanitary napkin include, but are not limited to slot coating, spraying, knife coating, extrusion coating, and transfer coating. The adhesives may also be foamed prior to application, such as by using commercially available equipment from the Nordson Corporation. Adhesives may be coated in continuous or in discrete patterns from emulsion or solution directly onto the product substrate or onto a release substrate to be subsequently transferred onto the article.

Figure 7:
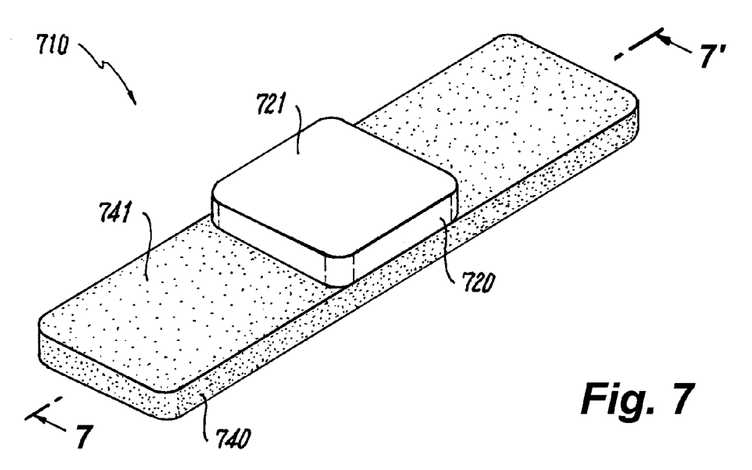
FIG. 7 is a perspective view of an absorbent article adapted for use as a wound covering in accordance with the present invention.
Figure 8:
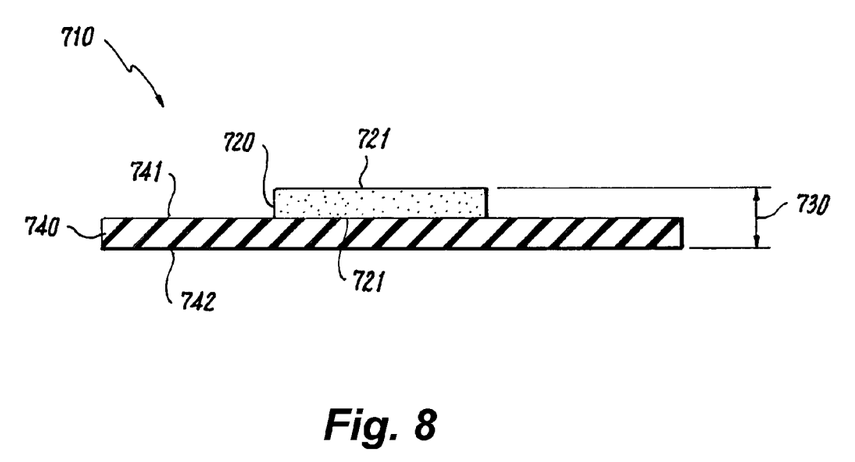
FIG. 8 is an end view of the embodiment shown in FIG. 7 as taken along section line 7-7' of FIG. 7.

FIGS. 7 and 8 show yet another embodiment of the present invention, an absorbent article 710 adapted for use as a wound covering comprising: a flexible backing layer 740 having a first surface 741 and a second surface 742 and a wound faceable aqueous liquid absorbing material 720 having a first surface 721 and a second surface 722 wherein the second surface 722 is disposed on at least a portion of the first surface 741 of the backing 740. The aqueous liquid absorbing material 720 comprises a homogeneous mixture of a hot melt adhesive and an aqueous liquid absorbing polymer, wherein said aqueous liquid absorbing polymer is present in the mixture in an amount greater than 1% by weight of the mixture. The article 710 is characterized by an absorbency greater than 5 g/g, a Gurley stiffness less than 250 mg and a caliper 730 less than 2 mm. Suitable materials for the flexible backing layer 740 include but are not limited to woven or knit fabrics, nonwoven webs, breathable polymeric films and apertured films. A particularly suitable material is polymeric film X6723 made by Tredegar, Inc. of Terre Haute, Ind.

Areas of the first surface 741 of the flexible backing web 740 adjacent to the aqueous liquid absorbing material 720 may be coated with an adhesive suitable for securing the bandage to skin. Suitable adhesives include but are not limited to hot melt, acrylate and rubber based adhesives. A particularly suitable material is hot melt adhesive HM3210 made by Bostich-Findley Inc. of Wawatosa, Wis.

Absorbent articles adapted for use as a wound covering with the aqueous liquid absorbing material of the present invention are thin extremely flexible and fully conformable to a user's body making the article comfortable in use while allowing freedom of movement, especially for areas of a body where a wide range of motion is desirable, such as hands, elbows or knees.

In an alternative embodiment (not shown), the aqueous liquid absorbing material is disposed on an adhesive layer contiguous to the first surface of the backing layer. Although not illustrated, the article adapted for use as a wound covering may be provided with conventional adhesive release tapes or tabs covering exposed adhesive and overlying the absorbent zone. In addition, a conventional wound release cover (not shown) may also be disposed on the first surface 721 of the absorbent zone 725 in order to provide a separate wound releasable layer between a wound and absorbent zone.

Figure 9:
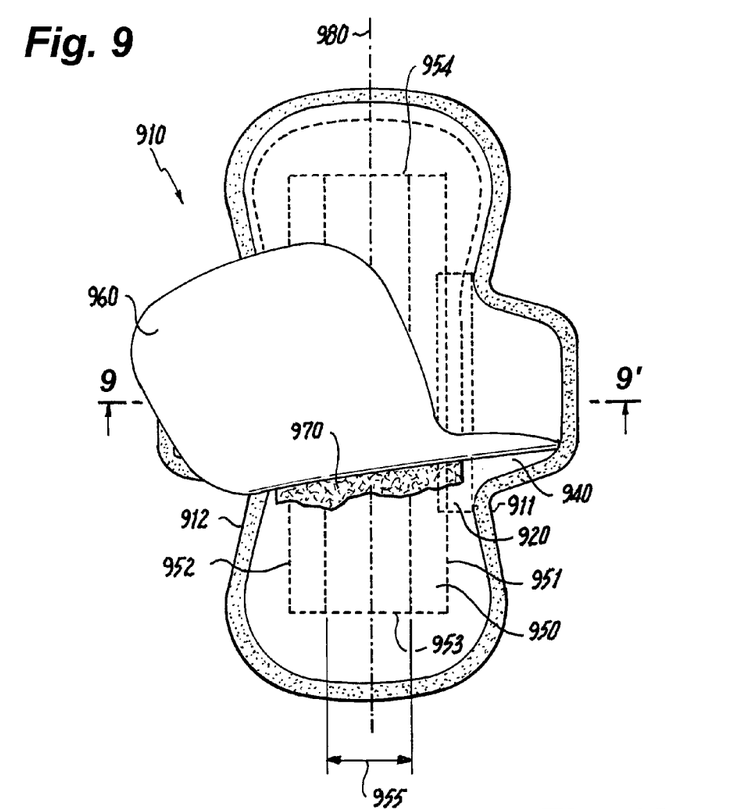
FIG. 9 is a top plan view of another absorbent article for feminine hygiene in accordance with the present invention, the body faceable layer of the article being partly removed to show the underlying structure.
Figure 10:
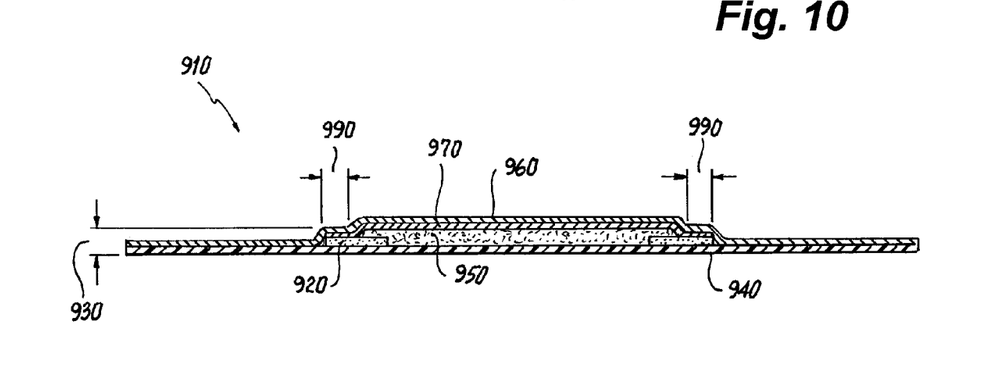
FIG. 10 is an end view of the embodiment shown in FIG. 9 as taken along section line 9-9' of FIG. 9.

Referring to FIGS. 9 and 10, there is shown another embodiment of the present invention, an absorbent article 910 for feminine hygiene adapted for placement in a crotch portion of an undergarment and having a longitudinal axis 980. The absorbent article 910 comprising a liquid permeable body faceable layer 960, a liquid impermeable garment faceable layer 940, an optional transfer layer 970 disposed adjacent said body faceable layer, an absorbent element 950 positioned between said transfer layer and said garment faceable layer and at least one peripheral zone 990 shown in FIG. 10. The absorbent element 950 has a longitudinally-extending central absorbent zone 955 aligned along the longitudinal axis 980 of said absorbent article 910 and has two opposing longitudinal edges 951, 952 parallel to and spaced apart from said longitudinal axis and two transverse edges 953, 954. The peripheral zone 990 is aligned adjacent to one of said longitudinal edges 951, 952 of absorbent element 950 and is spaced apart from and is inward from the side edges 911, 912 of the absorbent article 910. The peripheral zone 990 includes said body faceable layer 960, said optional transfer layer 970, said garment faceable layer 940 and aqueous liquid absorbing material 920. The aqueous liquid absorbing material 920 comprises a homogeneous mixture of a hot melt adhesive and an aqueous liquid absorbing polymer, wherein said aqueous liquid absorbing polymer is present in the mixture in an amount greater than 5% by weight of the mixture and said peripheral zone 990 is characterized by an absorbency greater than about 5 g/g, a Gurley stiffness less than 400 mg and a caliper 930 less than about 4 mm. The central absorbent zone 955 has a Gurley stiffness greater than the Gurley stiffness of the peripheral zone 990. In a accordance with this embodiment, the central absorbent zone has a Gurley stiffness less than 300 mg, preferably less than 200 mg and most preferably less than 100 mg, while the peripheral zone has a Gurley stiffness less than 200 mg, preferably less than 100 mg and most preferably less than 50 mg, with the proviso that the Gurley stiffness of the peripheral zone is less than the Gurley stiffness of the central absorbent zone. These differences between Gurley stiffness of the central absorbent zone and the peripheral absorbent zone result in an absorbent article that is flexible and conforms readily to the crotch portion of an undergarment while resisting bunching and twisting. Thus, absorbent articles according to this embodiment of the present invention provide at least two zones having different Gurley stiffness and which may have the same or different absorbency. This configuration allows flexibility in design of the absorbent article for achieving maximum consumer protection and comfort. In absorbent articles of the present invention, peripheral zone 990 preferably has a Gurley stiffness less than 200 mg, more preferably less than 100 mg and most preferable less than 50 mg. Preferably the difference in Gurley stiffness of the central absorbent zone and the peripheral zone is less than 500 mg, more preferably the difference is less than 200 mg, and most preferably the difference in Gurley stiffness of the central absorbent zone and the peripheral zone is at less than 50 mg. In a most preferred embodiment, the aqueous liquid absorbing material 920 is aligned parallel and adjacent to said absorbent element 950 and is partially covered by the absorbent element 950 as shown in FIG. 10.

This embodiment provides an extremely flexible, yet highly absorbent peripheral zone for absorbing fluid wicking along the sides of the absorbent article, thus reducing side leakage incidents in absorbent articles with this construction while remaining very conformable and comfortable in use. In accordance with this embodiment, the absorbent element may be formed from conventional materials used to form absorbent cores in sanitary napkins. Attachment means (not shown) are discussed above in the description of FIG. 5, 6.

A representative, non-limiting list, of absorbents useful in the absorbent element includes fibrous materials such as natural cellulosics, i.e. cotton and wood pulp; regenerated cellulosics, i.e. rayon and cellulose acetate; peat moss; hydrogel-forming polymers in the form of fibers or particles, commonly referred to as superabsorbents; and the like. Other absorbent materials such as foams may also be used. Non-limiting examples of suitable foam absorbents are open celled foams such as cellulosic or polyether foams. Blends of two or more types of absorbent materials may be used to optimize the performance of fluid management articles used in varying conditions. For example, the absorbent element may comprise a blend of absorbent materials and thermoplastic fibers, to provide structural integrity to the formed structure or for heat sealability to the liquid impermeable layer. Useful thermoplastic fibers are polyolefins, such as polypropylene and polyethylene fibers. The thermoplastic fibers may be bi-component or multi-component fibers having a first component having a first melting temperature and two or more additional components having different melting temperatures to that of the first melting temperature. Bi-component fibers are typically configured sheath-core or side-by-side. Suitable bi-component fibers include polyester/polyethylene and polypropylene/polyethylene.

In a preferred example the absorbent element is a material comprising cellulosic fibers and superabsorbent powder. The material preferably contains from about 40 to about 95 weight percent cellulosic fibers and, more preferably from about 60 to about 80 weight percent cellulosic fibers. Such a material may contain from about 5 to about 60 weight percent superabsorbent powder (SAP), preferably from about 20 to about 55 weight percent SAP, even more preferably from about 30 to about 45 weight percent SAP, and most preferably about 40 weight percent SAP.

Test Methods

Caliper:

As indicated above, the flexible aqueous liquid absorbing structure preferably has a thickness or caliper of about 4 mm or less. The apparatus required to measure the thickness of the sanitary napkin is a footed dial (thickness) gauge, Model No. ADP1116, available from B. C. Ames Company, of Waltham, Mass., with foot 29.6 mm diameter with stand, 56.7 gm. deadweight accurate to 0.0254 mm. A digital type apparatus is preferred. If the aqueous liquid absorbing structure sample is individually folded and/or wrapped, the sample is unwrapped and carefully flattened by hand prior to measurement. The foot of the gauge is raised and the sample is placed on the anvil such that the foot of the gauge is approximately centered to the sample (or in the location of interest on the sample of interest). When lowering the foot, care is taken to avoid allowing the foot to "drop" or that undue force is not applied. The read out is allowed to stabilize for approximately 5 seconds. The thickness reading is then taken. For each sample being tested, five (5) readings are recorded and an average is calculated and reported as the average caliper in mm.

Gurley Stiffness:

Gurley stiffness is one of many indices of softness. Gurley stiffness measures the bendability or flexibility of absorbent materials. The lower the Gurley stiffness value, the more flexible the material. The Gurley stiffness values are measured using a Gurley Stiffness Tester (Model No. 4171 D), manufactured by Gurley Precision Instruments of Troy, N.Y. The instrument measures the externally applied moment required to produce a given deflection of a test strip of specific dimensions fixed at one end and having a concentrated load applied to the other end. The results are obtained in "Gurley Stiffness" values in units of milligrams. The procedure for determining Gurley Stiffness is as follows:

Gurley Stiffness of Areas Containing Aqueous Liquid Absorbing Material

1. Locate Y areas of the product being tested that contain(s) the aqueous liquid absorbing material (ALAM) and mark these areas for identification (e.g. zone 1, zone 2, zone 3, etc.).
2. For each different area, die cut a rectangular sample 25.0 millimeters (mm) wide by 50.0 mm long.
   Note: If the dimensions of the ALAM area are less 25.0 by 50.0 (mm), die cut the next largest sample size possible by reducing the rectangle dimensions by increments of 12.0 mm. (Note the smallest size permitted by the Gurley tester is 12 mm wide by 24 mm long.)

4. Remove any release paper that may exist on the sample(s) and eliminate any stickiness that may exist by applying a layer of talcum powder and smoothing out any wrinkles.
5. Calibrate the Gurley tester per manufacturer's instructions.
6. Position the arm on the Gurley apparatus to the right.
7. According to the manufacturer's instructions, insert one sample at a time into the clamp and secure sample so the longer edge of the sample is parallel to the clamp.
8. Make sure the pendulum is steady at zero and move the switch to the left so that the entire sample moves across the pendulum.
9. Re-steady the pendulum at zero and move the switch to the right so that the entire sample moves across the pendulum.
10. Record the digital stiffness reading.
11. Repeat steps 1-10 until n=5 for each of Y zones identified (n=5 for zone 1, n=5 for zone 2, etc.).
12. Average the readings from each zone separately and report the lowest average reading as the stiffness value for the sample being tested.

Gurley Stiffness of Peripheral Zone and Central Absorbent Zone

1. Locate the area of the product being tested that contains the peripheral zone (PZ) and mark this area for identification (e.g. PZ-1).
2. Die cut a rectangular sample of the PZ 25.0 millimeters (mm) wide by 50.0 mm long.
   Note: If the dimensions of the PZ area are less 25.0 by 50.0 (mm), die cut the next largest sample size possible by reducing the rectangle dimensions by increments of 12.0 mm. (Note the smallest size permitted by the Gurley tester is 12 mm wide by 24 mm long.)
3. Locate the area of the product being tested that contains the central absorbent zone (CAZ) and mark this area for identification (e.g. CAZ-1).
4. Die cut a rectangular sample of the CAZ 25.0 millimeters (mm) wide by 50.0 mm long.
   Note: If the dimensions of the PZ area are less 25.0 by 50.0 (mm), die cut the CAZ sample to the same dimensions used for the PZ.
5. Remove any release paper that may exist on the sample(s) and eliminate any stickiness that may exist by applying a layer of talcum powder and smoothing out any wrinkles.
6. Calibrate the Gurley tester per manufacturer's instructions.
7. Position the arm on the Gurley apparatus to the right.
8. According to the manufacturer's instructions, insert one sample at a time into the clamp and secure sample so the longer edge of the sample is parallel to the clamp.
9. Make sure the pendulum is steady at zero and move the switch to the left so that the entire sample moves across the pendulum.
10. Re-steady the pendulum at zero and move the switch to the right so that the entire sample moves across the pendulum.
11. Record the digital stiffness reading.
12. Repeat steps 1-10 until n=5 for both PZ and CAZ samples.
13. Average the readings from the PZ samples and the CAZ samples separately and report the average calculated as the respective Gurley stiffness value for the CAZ and PZ samples being tested.

Absorbency:

The absorbency of the flexible aqueous liquid absorbing structure of the present invention and of products containing the structure is determined using the Tea Bag Test. The Tea Bag Test determines the free swell absorbency (Tea Bag Capacity) and results are expressed as grams of liquid absorbed per gram of dry aqueous liquid absorbing material (ALAM) being tested (g/g) The procedure for applying the Tea Bag Test to structures and articles of the present invention is as follows:

Determination of Dry Weight of ALAM:
1. Locate Y absorbent areas from the structure containing the aqueous liquid absorbing material (ALAM) or of the product being tested
2. Die cut a circular sample 60 mm in diameter or, if this size sample cannot be cut, cut a sample of equivalent area (2828 mm$^2$) from the ALAM.
3. Physically strip off as many layers from structure or product without disturbing the layer containing ALAM and weigh sample.
4. If further isolation of the ALAM can be obtained through chemical stripping, separate ALAM and weigh the remaining material.
5. The dry ALAM weight is found by subtracting the weight found in step 4 from the weight found in step 3. If step 4 was not possible then the dry ALAM weight is found in step 3.
6. Repeat steps 1-5 until n=5 for each of the Y areas.
7. Calculate the dry weight of ALAM for each area as the average of 5 measurements.
8. The lowest average is reported as the dry weight of ALAM (E).

Determination of Liquid Absorbed by Structure or Products with ALAM:
1. Locate the Y most absorbent areas from the structure containing the aqueous liquid absorbing material (ALAM) or of the product being tested
2. Die cut a circular sample 60 mm in diameter or, if this size sample cannot be cut, cut a sample of equivalent area (2828 mm$^2$) from the ALAM.
3. Die cut two 70×140-mm rectangular tea bag fabric pieces (tea bag fabric is Code 01234T9, produced by Ahlstrom-Dexter Corporation, Windsor Locks, Conn.).
4. Encase the die cut sample to be tested in one of the tea bags by folding and heat sealing the tea bag on 3 sides approximately 3 mm from the edge.

5. Fold and heat-seal the second tea bag in the same manner without sample; this will serve as a blank.
6. Record the weights of both tea bags.
7. Place both sealed tea bags into a container with 0.9% saline solution for 30 minutes (The tea bags should be submerged).
8. After 30 minutes, take the sample tea bag and the blank tea bag out of the solution and hang vertically with clips for 10 minutes (Be sure to clip the sample by the tea bag fabric only).
9. After 10 minutes, weigh and record the wet weights of both tea bags.
10. Calculate the gram/gram capacity of the sample as follows:

Absorbency or Tea Bag Capacity $(g/g) = (A-B-(C-D))/E$

Where A=Wet weight of sample
   B=Wet weight of blank
   C=Dry weight of sample with tea bag
   D=Dry weight of blank tea bag
   E=Dry weight of ALAM
11. Repeat steps 1-10 until n=5 for each of Y areas.
12. Calculate the absorbency for each area as the average of 5 measurements.
13. The highest average is reported as the tea bag capacity or Absorbency of the sample being tested.

While particular embodiments of the present invention have been illustrated and described, it would be obvious to those skilled in the art that various other changes and modifications can be made without departing from the spirit and scope of the invention.

We claim:

1. An absorbent article for feminine hygiene adapted for placement in a crotch portion of an undergarment, said absorbent article comprising: a liquid permeable body faceable layer; a liquid impermeable garment faceable layer and an aqueous liquid absorbing material between said body faceable layer and said garment faceable layer, said aqueous liquid absorbing material comprising a homogeneous mixture of a hot melt adhesive and an aqueous liquid absorbing polymer, wherein said aqueous liquid absorbing polymer is present in the mixture in an amount greater than 5% by weight of the mixture; said absorbent article being characterized by an absorbency greater than about 5 g/g, a Gurley stiffness less than 400 mg and a caliper less than about 4 mm; and
   wherein said aqueous liquid absorbing material has a first surface that is arranged in abutting relationship to said garment faceable layer and a second surface that is arranged in abutting relationship to a surface of said liquid permeable body faceable layer.

* * * * *